(12) United States Patent
Geusen et al.

(10) Patent No.: US 11,660,179 B2
(45) Date of Patent: May 30, 2023

(54) STENT GRAFT SYSTEMS WITH RESTRAINTS IN CHANNELS AND METHODS THEREOF

(71) Applicant: Endologix LLC, Irvine, CA (US)

(72) Inventors: Mark Geusen, Irvine, CA (US); Dale Ehnes, Forestville, CA (US); Jason Maggard, Santa Rosa, CA (US); Riley King, Santa Rosa, CA (US); Craig Welk, Irvine, CA (US)

(73) Assignee: Endologix LLC, Irvine, CA (US)

( * ) Notice: Subject to any disclaimer, the term of this patent is extended or adjusted under 35 U.S.C. 154(b) by 0 days.

(21) Appl. No.: 17/058,627

(22) PCT Filed: May 30, 2019

(86) PCT No.: PCT/US2019/034565
§ 371 (c)(1),
(2) Date: Nov. 24, 2020

(87) PCT Pub. No.: WO2019/232155
PCT Pub. Date: Dec. 5, 2019

(65) Prior Publication Data
US 2021/0205066 A1    Jul. 8, 2021

Related U.S. Application Data

(60) Provisional application No. 62/678,961, filed on May 31, 2018.

(51) Int. Cl.
*A61F 2/07*    (2013.01)
(52) U.S. Cl.
CPC .......... *A61F 2/07* (2013.01); *A61F 2002/072* (2013.01); *A61F 2210/0076* (2013.01);
(Continued)

(58) Field of Classification Search
CPC .................. A61F 2/07; A61F 2002/072; A61F 2210/0076; A61F 2220/0016; A61F 2220/0075; A61F 2220/0083
See application file for complete search history.

(56) References Cited

U.S. PATENT DOCUMENTS 6,270,520 B1    8/2001  Inoue
6,302,891 B1    10/2001 Nadal
(Continued)

FOREIGN PATENT DOCUMENTS

EP    2 841 014 B1    12/2017

OTHER PUBLICATIONS

International Search Report and Written Opinion dated Sep. 3, 2019, from application No. PCT/US2019/034565.
(Continued)

*Primary Examiner* — Suzette J Gherbi
(74) *Attorney, Agent, or Firm* — Foley & Lardner LLP

(57) ABSTRACT

A stent graft system includes a first layer of graft material, a second layer of graft material, one or more stent members, one or more reducing belts, and a release wire. The one or more stent members are located between the first layer of graft material and the second layer of graft material. The second layer of graft material is formed to have a corresponding channel over each of the one or more stent members. The one or more reducing belts each include a loop at both ends and each is located in a corresponding channel around a corresponding one of the stent members. The release wire passes through both loops of each of the one or more reducing belts when the one or more stent members are in a compressed state. Pulling the release wire allows for the stent graft system to radially expand.

12 Claims, 12 Drawing Sheets

(52) U.S. Cl.
CPC .............. *A61F 2220/0016* (2013.01); *A61F 2220/0075* (2013.01); *A61F 2220/0083* (2013.01)

(56) References Cited

U.S. PATENT DOCUMENTS

| | | | |
|---|---|---|---|
| 6,471,722 B1 | 10/2002 | Inoue | |
| 6,485,515 B2 | 11/2002 | Strecker | |
| 6,514,282 B1 | 2/2003 | Inoue | |
| 6,558,396 B1 | 5/2003 | Inoue | |
| 6,733,521 B2 | 5/2004 | Chobotov et al. | |
| 6,761,733 B2 | 7/2004 | Chobotov et al. | |
| 6,974,471 B2 | 12/2005 | Van Schie et al. | |
| 7,252,680 B2 | 8/2007 | Freitag | |
| 7,998,189 B2 | 8/2011 | Kolbel et al. | |
| 8,043,356 B2 | 10/2011 | Kolbel et al. | |
| 8,361,134 B2 | 1/2013 | Hartley et al. | |
| 8,377,113 B2 | 2/2013 | Hartley et al. | |
| 8,480,725 B2 | 7/2013 | Rasmussen et al. | |
| 8,597,346 B2 | 12/2013 | Hartley et al. | |
| 8,603,156 B2 | 12/2013 | Hartley et al. | |
| 8,728,148 B2 | 5/2014 | Roeder et al. | |
| 8,926,686 B2 | 1/2015 | King | |
| 8,968,384 B2 | 3/2015 | Pearson et al. | |
| 8,979,919 B2 | 3/2015 | Goddard et al. | |
| 9,226,814 B2 | 1/2016 | Jensen et al. | |
| 9,427,307 B2 | 8/2016 | Pearson et al. | |
| 9,427,317 B2 | 8/2016 | Styrc | |
| 9,498,361 B2 | 11/2016 | Roeder et al. | |
| 9,504,555 B2 | 11/2016 | Hartley et al. | |
| 9,707,072 B2 | 7/2017 | King | |
| 9,717,611 B2 | 8/2017 | Jensen et al. | |
| 9,724,217 B2 | 8/2017 | Hartley et al. | |
| 2002/0002397 A1* | 1/2002 | Martin ................ | A61F 2/07 623/1.12 |
| 2003/0004560 A1 | 1/2003 | Chobotov et al. | |
| 2003/0065378 A1 | 4/2003 | Chevillon et al. | |
| 2004/0138734 A1 | 7/2004 | Chobotov et al. | |
| 2006/0009833 A1 | 1/2006 | Chobotov et al. | |
| 2006/0095119 A1* | 5/2006 | Bolduc ................ | A61B 17/064 623/1.36 |
| 2007/0043425 A1 | 2/2007 | Hartley et al. | |
| 2009/0043377 A1* | 2/2009 | Greenberg ............ | A61F 2/856 623/1.35 |
| 2009/0099640 A1 | 4/2009 | Weng | |
| 2010/0049294 A1 | 2/2010 | Zukowski et al. | |
| 2010/0057196 A1 | 3/2010 | Pathak | |
| 2011/0125244 A1 | 5/2011 | Roeder et al. | |
| 2013/0053944 A1 | 2/2013 | Welch | |
| 2014/0121757 A1* | 5/2014 | Debruyne ............ | A61F 2/95 623/1.13 |
| 2014/0180378 A1 | 6/2014 | Roeder | |
| 2014/0194968 A1 | 7/2014 | Zukowski | |
| 2014/0257362 A1 | 9/2014 | Eidenschink | |
| 2014/0336745 A1 | 11/2014 | Barthold et al. | |
| 2016/0106532 A1 | 4/2016 | Jensen et al. | |
| 2016/0184118 A1 | 6/2016 | Faber et al. | |
| 2017/0165066 A1 | 6/2017 | Rothstein | |
| 2017/0165067 A1 | 6/2017 | Barajas-Torres et al. | |
| 2017/0189212 A1* | 7/2017 | Eller .................... | A61F 2/844 |
| 2017/0296325 A1* | 10/2017 | Marrocco ............ | A61F 2/07 |
| 2018/0042739 A1* | 2/2018 | Hagaman ............ | A61F 2/856 |
| 2018/0110609 A1 | 4/2018 | Ehnes et al. | |

OTHER PUBLICATIONS

International Preliminary Report on Patentability dated Dec. 10, 2020, from application No. PCT/US2019/034565.
Extended European Search Report dated Feb. 9, 2022, from application No. 19811286.4, 8 pages.

* cited by examiner

Position a stent graft system in a blood vessel with each stent member of a plurality of stent members held in a compressed state by a corresponding reducing belt of a plurality of reducing belts that is located at least partially in a corresponding channel between a second layer of graft material and a first layer of graft material — 200

Release the plurality of reducing belts to permit the plurality of stent members to expand from a compressed state to an uncompressed state — 210

Pull a release wire through and out of loops of one or more of the plurality of reducing belts — 220

FIG. 10

STENT GRAFT SYSTEMS WITH RESTRAINTS IN CHANNELS AND METHODS THEREOF

CROSS-REFERENCE TO RELATED PATENT APPLICATIONS

This application is a national stage application under 35 U.S.C. § 371 of International Application No. PCT/US2019/034565, filed May 30, 2019, which claims priority from U.S. Provisional Patent App. Ser. No. 62/678,961, filed May 31, 2018, the entire contents of each of which are incorporated by reference herein in their entirety.

FIELD

Embodiments disclosed herein relate generally to the field of endovascular stent graft systems. In particular, various embodiments relate to systems including stent grafts, and to methods of making such stent grafts, and to methods of using such stent grafts for treating aneurysms.

BACKGROUND

An aneurysm is a medical condition characterized by an expansion and weakening of the wall of an artery of a person. Aneurysms can develop at different sites within an artery. For example, thoracic aortic aneurysms or abdominal aortic aneurysms may manifest within a person's body. Such medical conditions are serious and potentially life threatening to a person, thereby requiring medical intervention to treat the condition. Existing systems and methods for treating such conditions include invasive surgical procedures with graft replacement of the affected vessel or body lumen.

Surgical procedures to treat aneurysms are associated with relatively high morbidity and mortality rates due to risk factors inherent to surgical repair of an artery or artery wall. Long and painful recoveries are often required, resulting in extensive medical costs. Because of the inherent risks and complexities of surgical repair of an aortic aneurysm, endovascular repair has become a widely used alternative therapy.

In endovascular repair, an expandable stent graft is placed within the damaged artery to reinforce the weakened portion of the wall of the artery. The stent graft is a fabric tube supported by scaffolds, or metal wire stents. The stent graft has several layers of material, such as polytetrafluorethylene (PTFE), surrounding the scaffolds. To perform the endovascular repair of the aneurysm, a surgeon makes a small incision, typically in the groin of a patient, and inserts a compressed stent graft delivery system through the incision, into the blood vessels, and to the location of the aneurysm. The stent graft is then allowed to expand within the artery to reinforce the damaged artery wall.

SUMMARY OF THE DISCLOSURE

Various embodiments provide for an enhancement in the compression and expansion of stent grafts for ease of insertion into one or more blood vessels of a patient. Various embodiments provide for endovascular stent graft compression by providing multiple layers of graft material surrounding stent members, creating channels with the graft material around each of the stent members, placing reducing belts over the stent members in the channels that are in between the layers of graft material, and providing a release wire through end loops of the reducing belts to easily release the reducing belts to allow the stent graft to expand when desired.

In some embodiments, a stent graft system includes a stent graft, one or more reducing belts such as sutures or wires, and a release wire or lock wire. In various embodiments, graft material for the stent graft is formed to have an integrated channel surrounding each of one or more stent members. In some embodiments, the one or more reducing belts are made of thread or wire and are each routed through a corresponding channel defined by a shape of the graft material around a corresponding stent member. In various embodiments, each reducing belt has a length that is less than a circumference of the fully expanded corresponding stent member but greater than a circumference of the stent member when in a compressed state, such that it is able to hold the stent member in a compressed state. In some embodiments, each reducing belt has a loop at both ends, and a release wire is configured to pass through both loops of the reducing belt when the stent graft is in a compressed state. Pulling the release wire from the loops of the reducing belts then allows for the stent graft to radially expand.

A stent graft system in accordance with an embodiment includes a first layer of graft material, a second layer of graft material, a stent member, and a reducing belt. The stent member is located between the first layer of graft material and the second layer of graft material. The reducing belt is located at least partially in a channel between the second layer of graft material and the first layer of graft material and around at least a portion of the stent member.

In various embodiments, the second layer of graft material has a shape that provides the channel between the second layer of graft material and the first layer of graft material. In various embodiments, the reducing belt has a length that is shorter than a circumference of the stent member when the stent member is fully expanded but longer than a circumference of the stent member when the stent member is in a compressed state. In some embodiments, the reducing belt includes loops and there is a corresponding loop of the loops at each end of the reducing belt. Also, in some embodiments, the stent graft system further includes a release wire passing through the loops of the reducing belt.

In various embodiments, the stent member is radially expandable from a compressed state to an uncompressed state, and the reducing belt is releasable to permit the stent member to expand from the compressed state to the uncompressed state. In some embodiments, the stent graft system further includes a second stent member located between the first layer of graft material and the second layer of graft material, and a second reducing belt located at least partially in a second channel between the second layer of graft material and the first layer of graft material and around at least a portion of the second stent member.

In some embodiments, the second layer of graft material has a shape that provides the second channel between the second layer of graft material and the first layer of graft material. Also, in some embodiments, the reducing belt includes loops and the second reducing belt includes loops, and the stent graft system further includes a release wire passing through the loops of the reducing belt and through the loops of the second reducing belt. In some embodiments, the stent graft system further includes a pleat in the second layer of graft material between the stent member and the second stent member.

A method in accordance with an embodiment of manufacturing a stent graft system includes placing a plurality of stent members on a first layer of graft material, placing at least partially around each stent member of the plurality of stent members a respective spacer of a plurality of spacers, encapsulating at least a portion of each spacer of the plurality of spacers using a second layer of graft material, and removing each of the plurality of spacers from a respective opening in the second layer of graft material to leave a respective channel around each stent member of the plurality of stent members between the second layer of graft material and the first layer of graft material. In various embodiments, each spacer of the plurality of spacers comprises a tube.

In various embodiments, the method further includes placing at least partially around each stent member of the plurality of stent members in the respective channel a respective reducing belt of a plurality of reducing belts. In some embodiments, each reducing belt of the plurality of reducing belts comprises thread. In some embodiments, each of the plurality of reducing belts includes loops, and the method further includes placing a release wire through the loops of each of the plurality of reducing belts to hold the plurality of stent members in a radially compressed state. In some embodiments, the reducing belts are positioned such that ends of each reducing belt of the plurality of reducing belts extend out of a respective opening in the second layer of graft material.

In various embodiments, the method further includes axially compressing the second layer of graft material to form pleats in the second layer of graft material, applying heat to set creases for the pleats in the second layer of graft material, and pulling the second layer of graft material to axially uncompress the second layer of graft material after the pleats have been thermally set. In some embodiments, the applying of the heat includes baking the second layer of graft material in an oven to set the creases for the pleats in the second layer of graft material.

A method in accordance with an embodiment allows for using a stent graft system. The stent graft system includes a first layer of graft material, a second layer of graft material, a plurality of stent members, and a plurality of reducing belts. The method includes positioning the stent graft system in a blood vessel with each stent member of the plurality of stent members held in a compressed state by a corresponding reducing belt of the plurality of reducing belts that is located at least partially in a corresponding channel between the second layer of graft material and the first layer of graft material, and releasing the plurality of reducing belts to permit the plurality of stent members to expand from the compressed state to an uncompressed state. In some embodiments, the releasing of the plurality of reducing belts includes pulling a release wire through and out of loops of one or more of the plurality of reducing belts.

BRIEF DESCRIPTION OF THE DRAWINGS

FIG. 10 is a flowchart of a method for deploying a stent graft system in accordance with an embodiment in a blood vessel.

DETAILED DESCRIPTION

Figure 1:
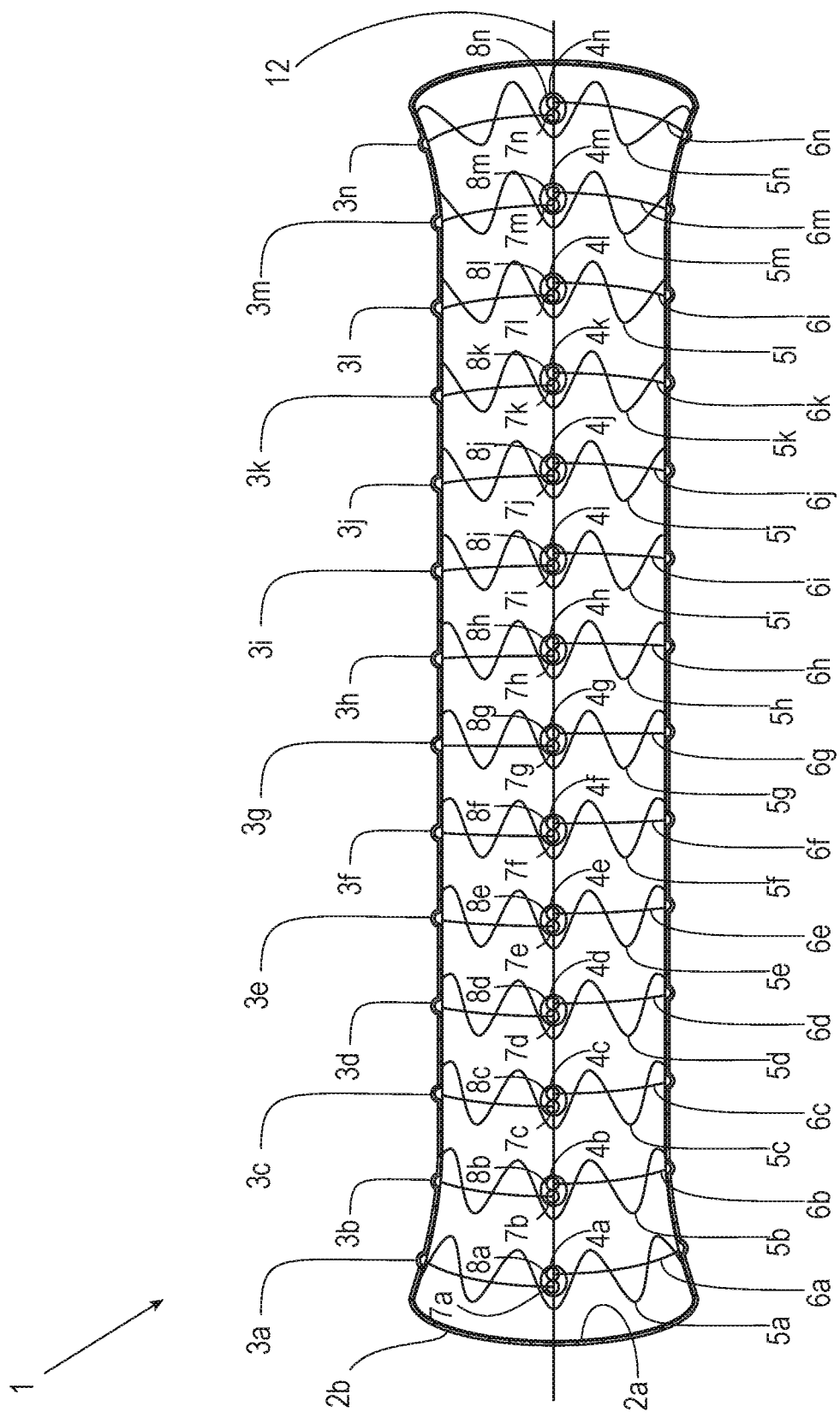
FIG. 1 shows a stent graft system in accordance with an embodiment.

In the following detailed description, reference is made to the accompanying drawings, which form a part hereof. In the drawings, similar symbols typically identify similar items, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Various embodiments provide for an enhancement in the method of compression and expansion of stent grafts by providing reducing belts, such as sutures or wires, circumferentially around stent members within channels formed by graft material. Various embodiments provide for stent graft compression and expansion enhancements by (1) providing multiple layers of graft material surrounding stent members, (2) placing circumferential reducing belts over the stent members in between the layers of graft material, and (3) providing a release wire through ends of the reducing belts to easily release the reducing belts to allow for radial expansion of the stent members when desired.

Various embodiments provide for a stent graft system with circumferential reducing belts surrounding stent members. In various embodiments, the reducing belts are each shorter in length than a circumference of a corresponding stent member when the stent member is in a fully expanded state, but longer in length than a circumference of the corresponding stent member when the stent member is in a compressed state. The reducing belts surround the stent members when the stent members are in a compressed state. In various embodiments, the reducing belts each have a loop at both of ends of the reducing belt. A release wire passes through both loops of each reducing belt surrounding each stent member to maintain a compression of the stent members. In various embodiments, after insertion of the stent graft system into a blood vessel, the release wire is removed from the loops of the reducing belts to allow for expansion of the stent members.

FIG. 1 shows a stent graft system 1 in accordance with an embodiment. The stent graft system 1 includes a first layer of graft material 2*a*, a second layer of graft material 2*b*, stent members 5*a*, 5*b*, 5*c*, 5*d*, 5*e*, 5*f*, 5*g*, 5*h*, 5*i*, 5*j*, 5*k*, 5*l*, 5*m*, 5*n*, reducing belts 6*a*, 6*b*, 6*c*, 6*d*, 6*e*, 6*f*, 6*g*, 6*h*, 6*i*, 6*j*, 6*k*, 6*l*, 6*m*, 6n, and a release wire 12. The stent members 5a, 5b, 5c, 5d, 5e, 5f, 5g, 5h, 5i, 5j, 5k, 5l, 5m, 5n are located between the first layer of graft material 2a and the second layer of graft material 2b. The second layer of graft material 2b is formed to have a shape that provides a corresponding channel 3a, 3b, 3c, 3d, 3e, 3f, 3g, 3h, 3i, 3j, 3k, 3l, 3m, 3n around each of the stent members 5a, 5b, 5c, 5d, 5e, 5f, 5g, 5h, 5i, 5j, 5k, 5l, 5m, 5n. In various embodiments, the corresponding channel 3a, 3b, 3c, 3d, 3e, 3f, 3g, 3h, 3i, 3j, 3k, 3l, 3m, 3n around each of the stent members 5a, 5b, 5c, 5d, 5e, 5f, 5g, 5h, 5i, 5j, 5k, 5l, 5m, 5n is a circumferential channel.

The reducing belts 6a, 6b, 6c, 6d, 6e, 6f, 6g, 6h, 6i, 6j, 6k, 6l, 6m, 6n each include a corresponding first loop 7a, 7b, 7c, 7d, 7e, 7f, 7g, 7h, 7i, 7j, 7k, 7l, 7m, 7n at one end and a corresponding second loop 8a, 8b, 8c, 8d, 8e, 8f, 8g, 8h, 8i, 8j, 8k, 8l, 8m, 8n at the other end. Each of the reducing belts 6a, 6b, 6c, 6d, 6e, 6f, 6g, 6h, 6i, 6j, 6k, 6l, 6m, 6n is located in a corresponding channel 3a, 3b, 3c, 3d, 3e, 3f, 3g, 3h, 3i, 3j, 3k, 3l, 3m, 3n around a corresponding one of the stent members 5a, 5b, 5c, 5d, 5e, 5f, 5g, 5h, 5i, 5j, 5k, 5l, 5m, 5n.

The first loop 7a, 7b, 7c, 7d, 7e, 7f, 7g, 7h, 7i, 7j, 7k, 7l, 7m, 7n and the second loop 8a, 8b, 8c, 8d, 8e, 8f, 8g, 8h, 8i, 8j, 8k, 8l, 8m, 8n of each of the reducing belts 6a, 6b, 6c, 6d, 6e, 6f, 6g, 6h, 6i, 6j, 6k, 6l, 6m, 6n extend out of a corresponding opening 4a, 4b, 4c, 4d, 4e, 4f, 4g, 4h, 4i, 4j, 4k, 4l, 4m, 4n in the second layer of graft material 2b. The release wire 12 passes through the first loop 7a, 7b, 7c, 7d, 7e, 7f, 7g, 7h, 7i, 7j, 7k, 7l, 7m, 7n and the second loop 8a, 8b, 8c, 8d, 8e, 8f, 8g, 8h, 8i, 8j, 8k, 8l, 8m, 8n of each of the reducing belts 6a, 6b, 6c, 6d, 6e, 6f, 6g, 6h, 6i, 6j, 6k, 6l, 6m, 6n when the stent members 5a, 5b, 5c, 5d, 5e, 5f, 5g, 5h, 5i, 5j, 5k, 5l, 5m, 5n are in a compressed state.

In various embodiments, each of the reducing belts 6a, 6b, 6c, 6d, 6e, 6f, 6g, 6h, 6i, 6j, 6k, 6l, 6m, 6n has a length that is shorter than a circumference of the corresponding stent member 5a, 5b, 5c, 5d, 5e, 5f, 5g, 5h, 5i, 5j, 5k, 5l, 5m, 5n when the corresponding stent member 5a, 5b, 5c, 5d, 5e, 5f, 5g, 5h, 5i, 5j, 5k, 5l, 5m, 5n is fully expanded but longer than a circumference of the corresponding stent member 5a, 5b, 5c, 5d, 5e, 5f, 5g, 5h, 5i, 5j, 5k, 5l, 5m, 5n when the stent member 5a, 5b, 5c, 5d, 5e, 5f, 5g, 5h, 5i, 5j, 5k, 5l, 5m, 5n is in a compressed state. This allows for the reducing belts 6a, 6b, 6c, 6d, 6e, 6f, 6g, 6h, 6i, 6j, 6k, 6l, 6m, 6n to maintain the stent members 5a, 5b, 5c, 5d, 5e, 5f, 5g, 5h, 5i, 5j, 5k, 5l, 5m, 5n in a compressed state until the release wire 12 is pulled. Once the release wire 12 is pulled, the stent members 5a, 5b, 5c, 5d, 5e, 5f, 5g, 5h, 5i, 5j, 5k, 5l, 5m, 5n expand to an expanded or uncompressed state.

The stent graft system 1 is a hollow tubular device having the first layer of graft material 2a forming a tubular wall and defining an open lumen. While stent graft system 1 as seen in FIG. 1 is depicted as being substantially tubular, one knowledgeable in the art would understand that stent graft system 1 may be of any shape that is suitable for delivery to and placement in a target site of a patient. In various embodiments, the first and second layers of graft material 2a, 2b comprise graft material that is made from one or more polymers or other suitable materials. In some embodiments, the first and second layers of graft material 2a, 2b are made of polytetrafluoroethylene (PTFE). In some embodiments, the first and second layers of graft material 2a, 2b are made of expanded polytetrafluoroethylene (ePTFE).

In some embodiments, the stent members 5a, 5b, 5c, 5d, 5e, 5f, 5g, 5h, 5i, 5j, 5k, 5l, 5m, 5n, are connected to each other as a single stent, while in some embodiments they are separate from each other. Each of the stent members 5a, 5b, 5c, 5d, 5e, 5f, 5g, 5h, 5i, 5j, 5k, 5l, 5m, 5n may be made, for example, from stainless steel, a nickel titanium alloy (NiTi) such as NITINOL, or any other suitable material, including but not limited to, a cobalt-based alloy such as ELGILOY, platinum, gold, titanium, tantalum, niobium, and/or combinations thereof. In the embodiment shown, each of the stent members 5a, 5b, 5c, 5d, 5e, 5f, 5g, 5h, 5i, 5j, 5k, 5l, 5m, 5n is radially expandable from a compressed state to an expanded or uncompressed state. The stent members 5a, 5b, 5c, 5d, 5e, 5f, 5g, 5h, 5i, 5j, 5k, 5l, 5m, 5n may be balloon expandable or self-expandable. While the embodiment shown in FIG. 1 shows a certain number of stent members 5a, 5b, 5c, 5d, 5e, 5f, 5g, 5h, 5i, 5j, 5k, 5l, 5m, 5n, it should be appreciated that, in various embodiments, any number of stent members may be used. In the embodiment shown, portions of the stent graft system 1 are flared outwardly at both proximal and distal ends, but in various other embodiments a stent graft system may be uniform across its length.

Each of the stent members 5a, 5b, 5c, 5d, 5e, 5f, 5g, 5h, 5i, 5j, 5k, 5l, 5m, 5n is compressed by the corresponding reducing belt 6a, 6b, 6c, 6d, 6e, 6f, 6g, 6h, 6i, 6j, 6k, 6l, 6m, 6n to circumferentially reduce the diameter of stent members 5a, 5b, 5c, 5d, 5e, 5f, 5g, 5h, 5i, 5j, 5k, 5l, 5m, 5n and hold them in a compressed state. In various embodiments, the reducing belts 6a, 6b, 6c, 6d, 6e, 6f, 6g, 6h, 6i, 6j, 6k, 6l, 6m, 6n are sutures, threads, wires, or the like.

The reducing belts 6a, 6b, 6c, 6d, 6e, 6f, 6g, 6h, 6i, 6j, 6k, 6l, 6m, 6n surround the corresponding stent members 5a, 5b, 5c, 5d, 5e, 5f, 5g, 5h, 5i, 5j, 5k, 5l, 5m, 5n and are each located in the corresponding channel 3a, 3b, 3c, 3d, 3e, 3f, 3g, 3h, 3i, 3j, 3k, 3l, 3m, 3n between the first layer of graft material 2a and the second layer of graft material 2b. The ends of each of the reducing belts 6a, 6b, 6c, 6d, 6e, 6f, 6g, 6h, 6i, 6j, 6k, 6l, 6m, 6n have the corresponding first loop 7a, 7b, 7c, 7d, 7e, 7f, 7g, 7h, 7i, 7j, 7k, 7l, 7m, 7n and second loop 8a, 8b, 8c, 8d, 8e, 8f, 8g, 8h, 8i, 8j, 8k, 8l, 8m, 8n that extend out of the corresponding opening 4a, 4b, 4c, 4d, 4e, 4f, 4g, 4h, 4i, 4j, 4k, 4l, 4m, 4n in the second layer of graft material 2b. The release wire 12 passes through the first loop 7a, 7b, 7c, 7d, 7e, 7f, 7g, 7h, 7i, 7j, 7k, 7l, 7m, 7n and the second loop 8a, 8b, 8c, 8d, 8e, 8f, 8g, 8h, 8i, 8j, 8k, 8l, 8m, 8n of each of the reducing belts 6a, 6b, 6c, 6d, 6e, 6f, 6g, 6h, 6i, 6j, 6k, 6l, 6m, 6n and extends outward on both the proximal and distal end of the stent graft system 1. When release wire 12 is pulled, each of the reducing belts 6a, 6b, 6c, 6d, 6e, 6f, 6g, 6h, 6i, 6j, 6k, 6l, 6m, 6n releases its compression on its corresponding stent member 5a, 5b, 5c, 5d, 5e, 5f, 5g, 5h, 5i, 5j, 5k, 5l, 5m, 5n and the stent graft system 1 is allowed to radially expand.

Figure 2:
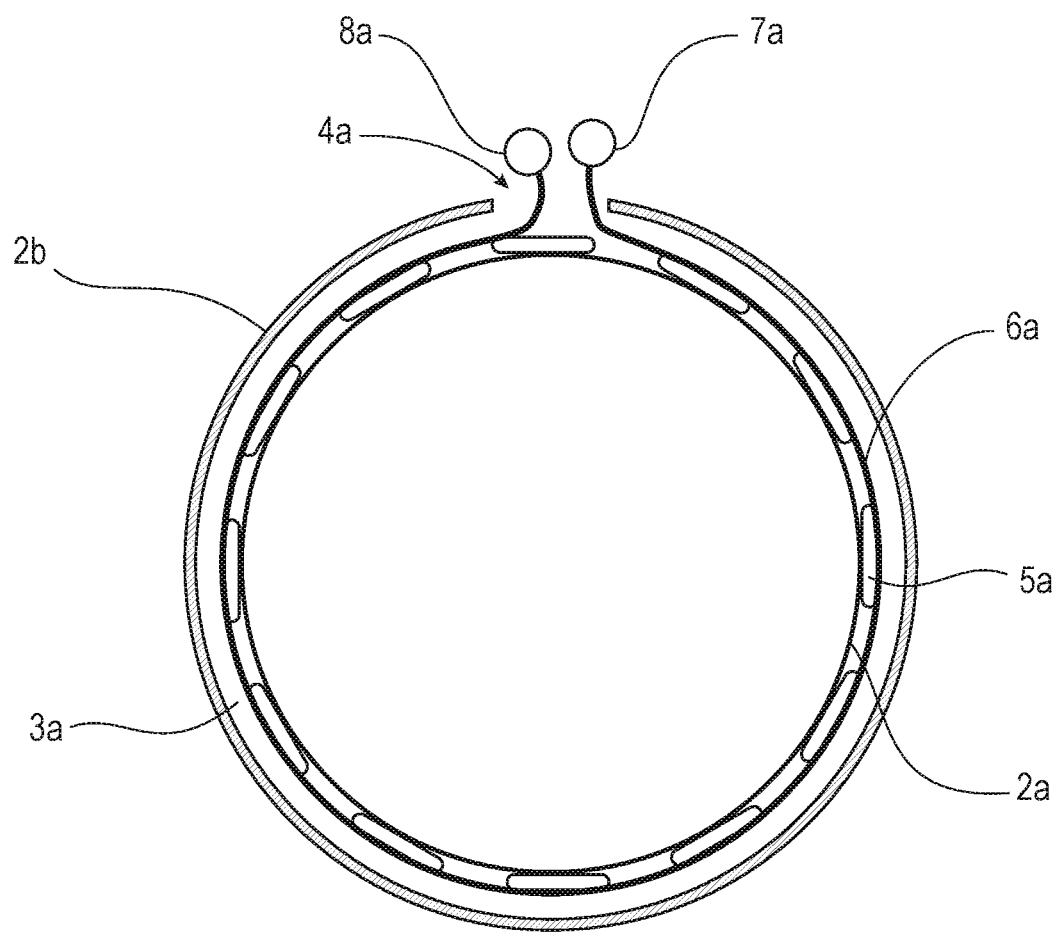
FIG. 2 shows a section of a stent graft system in accordance with an embodiment.

FIG. 2 shows a section of the stent graft system 1 of FIG. 1 in accordance with an embodiment. The stent member 5a is located between the first layer of graft material 2a and the second layer of graft material 2b. The second layer of graft material 2b is formed to provide the corresponding channel 3a around the stent member 5a. The reducing belt 6a has the first loop 7a at a first end and the second loop 8a at a second end and can extend out of the opening 4a in the second layer of graft material 2b. The reducing belt 6a is located in the channel 3a around the stent member 5a. The release wire 12 (refer to FIG. 1) is able to pass through the first loop 7a and the second loop 8a of the reducing belt 6a to cause the reducing belt 6a to hold the stent member 5a in a compressed state.

Figure 3:
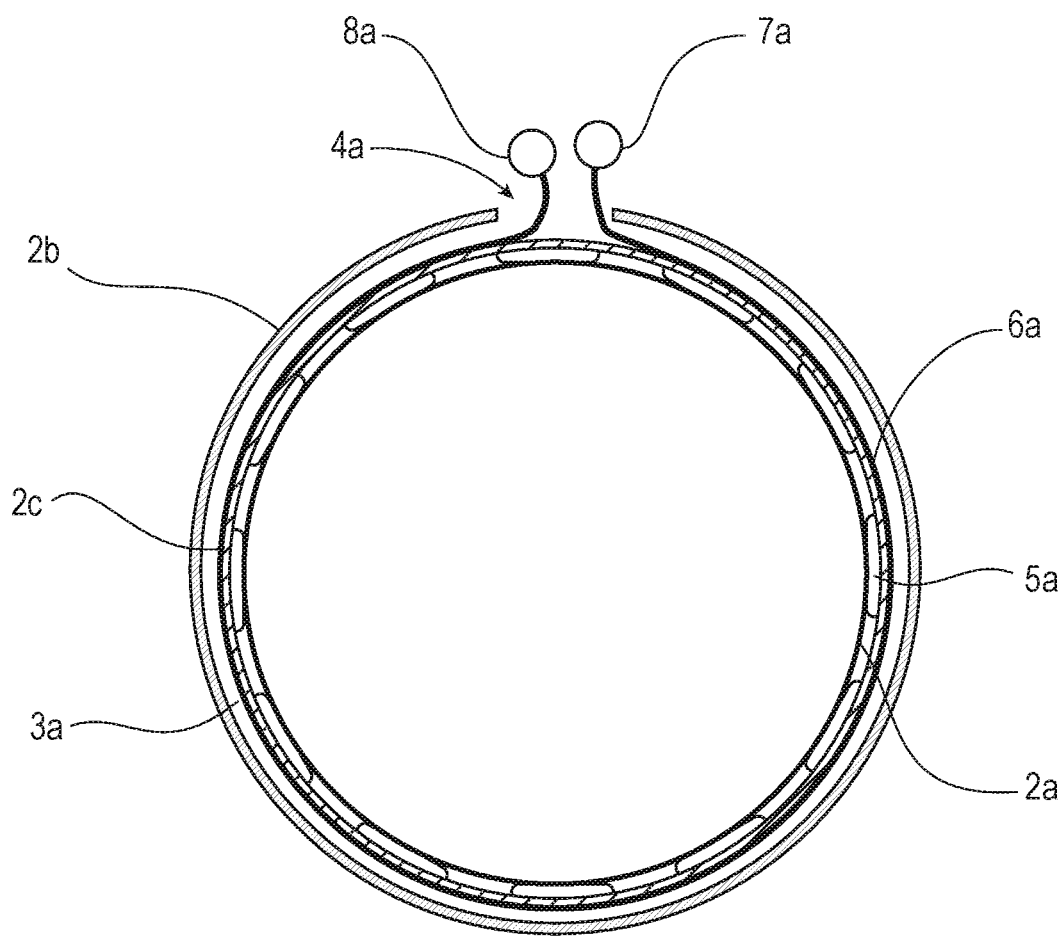
FIG. 3 shows a section of a stent graft system in accordance with an embodiment.

FIG. 3 shows a section of a stent graft system that is similar to FIG. 2 with like reference labels referencing like elements, but further includes an additional third layer of graft material 2c that is between the stent member 5a and the second layer of graft material 2b. Of course, in various other embodiments, any number of layers of graft material may be used. The channel 3a in the embodiment of FIG. 3 is between the second layer of graft material 2b and the third layer of graft material 2c.

Figure 4:
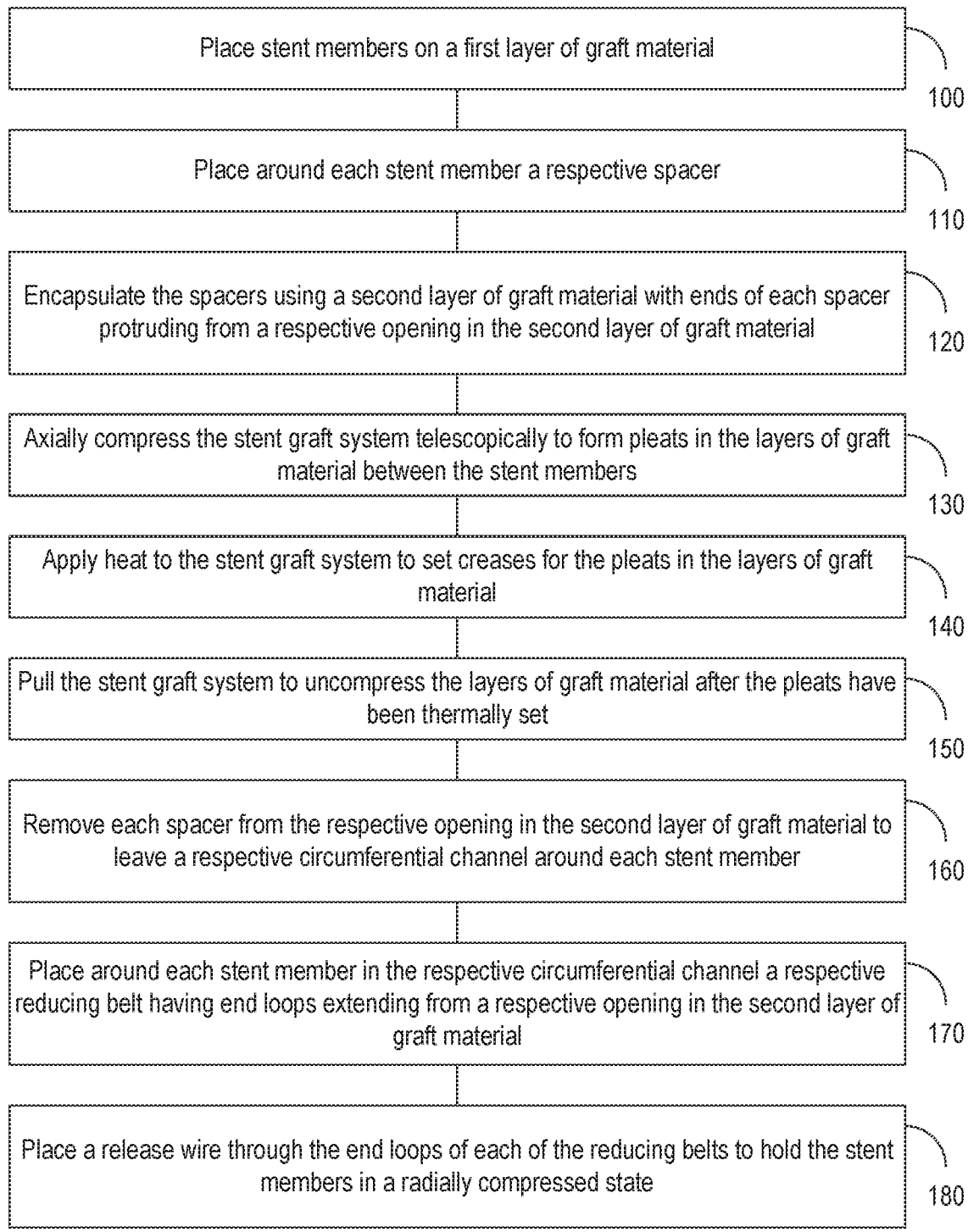
FIG. 4 is a flowchart of a method for making a stent graft system in accordance with an embodiment.
Figure 5:
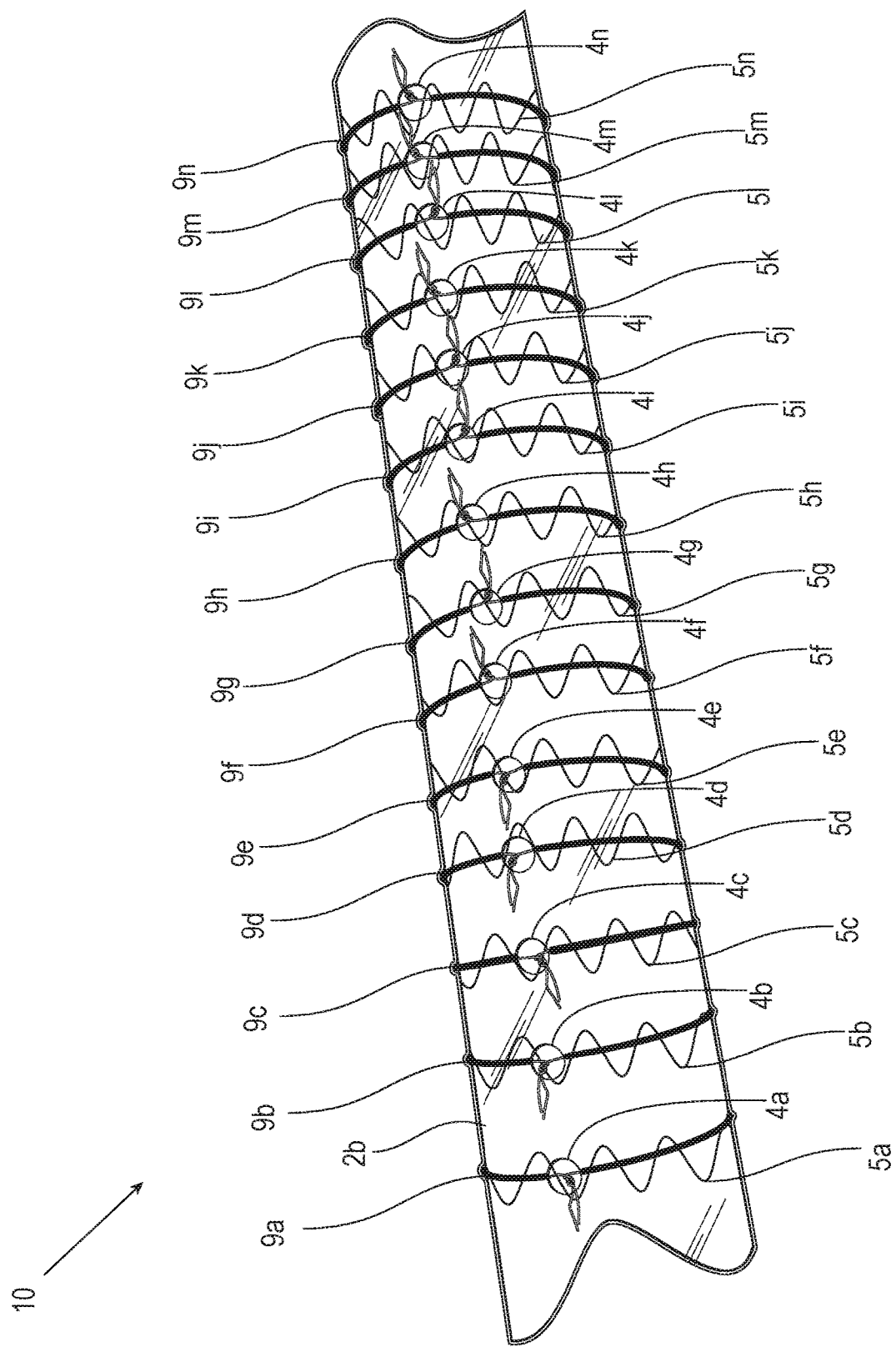
FIG. 5 shows a stent graft system during a stage of manufacture in accordance with an embodiment.
Figure 6:
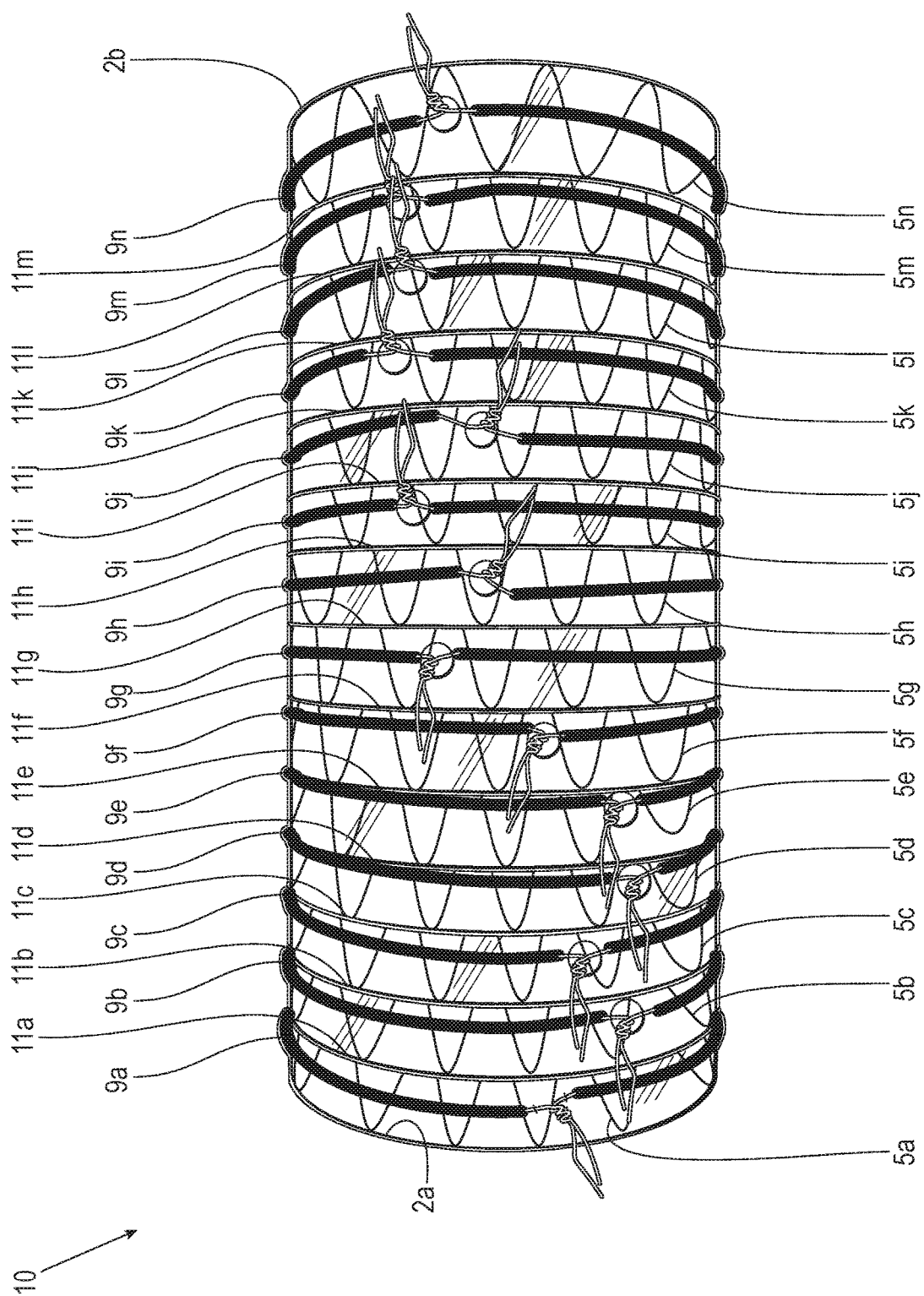
FIG. 6 shows a stent graft system during another stage of manufacture in accordance with an embodiment.
Figure 7:
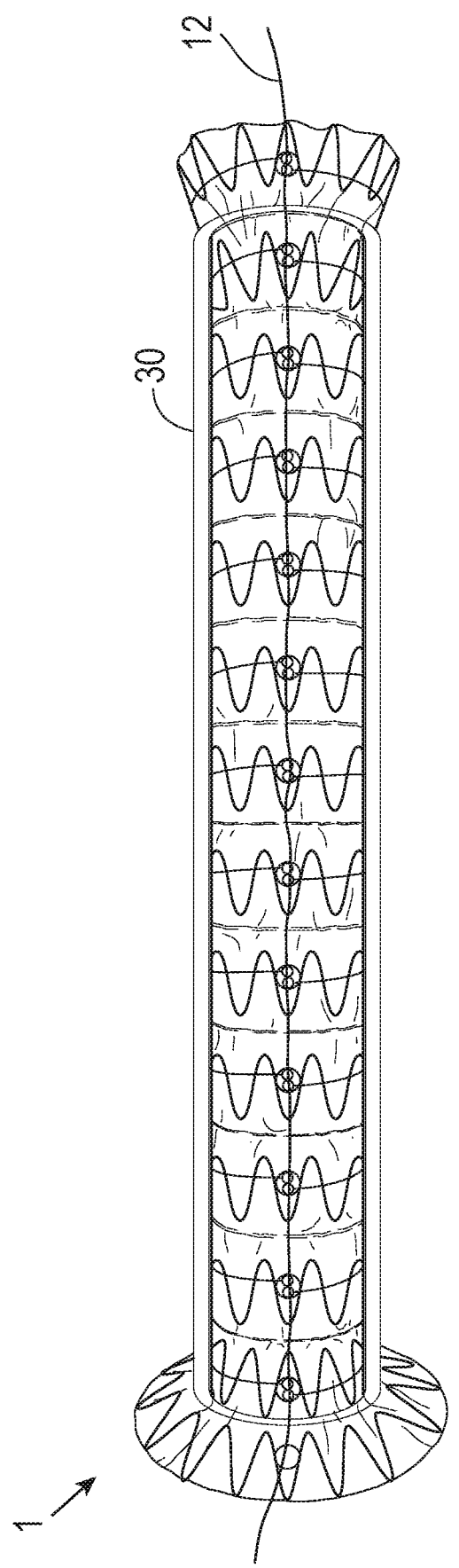
FIG. 7 shows a stent graft system during yet another stage of manufacture in accordance with an embodiment.

FIG. 4 is a flowchart of a method for making a stent graft system in accordance with an embodiment. FIGS. 5 and 6 show a stent graft system 10 during various stages of manufacture in accordance with an embodiment that is manufactured to become the stent graft system 1 of FIG. 1. A stage of the manufacturing in accordance with various embodiments is also shown in FIG. 7. With reference to FIGS. 1, 4, 5, and 6, in step 100 stent members are placed on a first layer of graft material. For example, the stent members 5a, 5b, 5c, 5d, 5e, 5f, 5g, 5h, 5i, 5j, 5k, 5l, 5m, 5n are placed on the first layer of graft material 2a. In step 110, around each stent member is placed a respective spacer. For example, around each stent member 5a, 5b, 5c, 5d, 5e, 5f, 5g, 5h, 5i, 5j, 5k, 5l, 5m, 5n is placed a respective spacer 9a, 9b, 9c, 9d, 9e, 9f, 9g, 9h, 9i, 9j, 9k, 9l, 9m, 9n. In various embodiments, each of the spacers 9a, 9b, 9c, 9d, 9e, 9f, 9g, 9h, 9i, 9j, 9k, 9l, 9m, 9n includes a tube or the like. In various embodiments, each of the spacers 9a, 9b, 9c, 9d, 9e, 9f, 9g, 9h, 9i, 9j, 9k, 9l, 9m, 9n is a Kapton tube or the like. In various embodiments, each of the spacers 9a, 9b, 9c, 9d, 9e, 9f, 9g, 9h, 9i, 9j, 9k, 9l, 9m, 9n comprises a polyimide or the like.

In step 120, the spacers are encapsulated using a second layer of graft material with ends of each spacer protruding from a respective opening in the second layer of graft material. For example, the spacers 9a, 9b, 9c, 9d, 9e, 9f, 9g, 9h, 9i, 9j, 9k, 9l, 9m, 9n are encapsulated using the second layer of graft material 2b with ends of each of the spacers 9a, 9b, 9c, 9d, 9e, 9f, 9g, 9h, 9i, 9j, 9k, 9l, 9m, 9n protruding from a respective opening 4a, 4b, 4c, 4d, 4e, 4f, 4g, 4h, 4i, 4j, 4k, 4l, 4m, 4n in the second layer of graft material 2b.

In step 130, the stent graft system is axially compressed telescopically to form pleats in the layers of graft material between the stent members. For example, the stent graft system 10 is axially compressed telescopically to form pleats 11a, 11b, 11c, 11d, 11e, 11f, 11g, 11h, 11i, 11j, 11k, 11l, 11m (see FIG. 6) in the second layer of graft material 2b between the respective stent members 5a, 5b, 5c, 5d, 5e, 5f, 5g, 5h, 5i, 5j, 5k, 5l, 5m, 5n. With reference to FIGS. 4 and 6, in step 140, heat is applied to the stent graft system to set creases for the pleats in the layers of graft material. For example, heat is applied to the stent graft system 10 while it is telescopically compressed to set creases for the pleats 11a, 11b, 11c, 11d, 11e, 11f, 11g, 11h, 11i, 11j, 11k, 11l, 11m.

In various embodiments, the applying of heat is performed by applying an iron to the pleats 11a, 11b, 11c, 11d, 11e, 11f, 11g, 11h, 11i, 11j, 11k, 11l, 11m to set the creases for the pleats 11a, 11b, 11c, 11d, 11e, 11f, 11g, 11h, 11i, 11j, 11k, 11l, 11m. In some embodiments the applying of heat is performed by placing the stent graft system 10 in an oven to bake the stent graft system 10 for a predetermined time period to thermally lock in the creases for the pleats 11a, 11b, 11c, 11d, 11e, 11f, 11g, 11h, 11i, 11j, 11k, 11l, 11m. In various embodiments, the stent graft system 10 is longitudinally compressed to form the plurality of circumferential pleats 11a, 11b, 11c, 11d, 11e, 11f, 11g, 11h, 11i, 11j, 11k, 11l, 11m with a predetermined orientation. Each of the pleats 11a, 11b, 11c, 11d, 11e, 11f, 11g, 11h, 11i, 11j, 11k, 11l, 11m may involve a creased or folded surface of the graft material, which are formed in areas between the locations of each of the stent members 5a, 5b, 5c, 5d, 5e, 5f, 5g, 5h, 5i, 5j, 5k, 5l, 5m, 5n. In various embodiments, each of the plurality of circumferential pleats 11a, 11b, 11c, 11d, 11e, 11f, 11g, 11h, 11i, 11j, 11k, 11l, 11m is disposed in between the crowns formed by two respective stent members of the stent members 5a, 5b, 5c, 5d, 5e, 5f, 5g, 5h, 5i, 5j, 5k, 5l, 5m, 5n.

In step 150, the stent graft system is pulled to uncompress the layers of graft material after the pleats have been thermally set. For example, the stent graft system 10 of FIG. 6 is pulled in a longitudinal direction to uncompress the stent graft system 10 in a longitudinal direction after the pleats 11a, 11b, 11c, 11d, 11e, 11f, 11g, 11h, 11i, 11j, 11k, 11l, 11m have been thermally set. With reference to FIGS. 1, 4, 5, 6, and 7, in step 160, each of the spacers is removed from the respective opening in the second layer of graft material to leave a respective circumferential channel around each stent member. For example, each of the spacers 9a, 9b, 9c, 9d, 9e, 9f, 9g, 9h, 9i, 9j, 9k, 9l, 9m, 9n of the stent graft system 10 is removed from the respective opening 4a, 4b, 4c, 4d, 4e, 4f, 4g, 4h, 4i, 4j, 4k, 4l, 4m, 4n in the second layer of graft material 2b to leave the respective channel 3a, 3b, 3c, 3d, 3e, 3f, 3g, 3h, 3i, 3j, 3k, 3l, 3m, 3n around each of the stent members 5a, 5b, 5c, 5d, 5e, 5f, g, 5h, 5i, 5j, 5k, 5l, 5m, 5n as in the resulting stent graft system 1.

With reference to FIGS. 1, 4, and 7, in step 170, around each stent member in the respective channel is placed a respective reducing belt having end loops extending from a respective opening in the second layer of graft material. For example, around each of the stent members 5a, 5b, 5c, 5d, 5e, 5f, 5g, 5h, 5i, 5j, 5k, 5l, 5m, 5n in the corresponding channel 3a, 3b, 3c, 3d, 3e, 3f, 3g, 3h, 3i, 3j, 3k, 3l, 3m, 3n is placed a respective one of the reducing belts 6a, 6b, 6c, 6d, 6e, 6f, 6g, 6h, 6i, 6j, 6k, 6l, 6m, 6n having end loops extending from a respective opening 4a, 4b, 4c, 4d, 4e, 4f, 4g, 4h, 4i, 4j, 4k, 4l, 4m, 4n in the second layer of graft material 2b. In step 180, a release wire is placed through the end loops of each of the reducing belts to hold the stent members in a radially compressed state. For example, the release wire 12 is placed through the corresponding first loop 7a, 7b, 7c, 7d, 7e, 7f, 7g, 7h, 7i, 7j, 7k, 7l, 7m, 7n and the corresponding second loop 8a, 8b, 8c, 8d, 8e, 8f, 8g, 8h, 8i, 8j, 8k, 8l, 8m, 8n of each of the reducing belts 6a, 6b, 6c, 6d, 6e, 6f, 6g, 6h, 6i, 6j, 6k, 6l, 6m, 6n to hold the stent members 5a, 5b, 5c, 5d, 5e, 5f, 5g, 5h, 5i, 5j, 5k, 5l, 5m, 5n in a radially compressed state. FIG. 7 shows an example of a manufacturing stage for inserting the release wire 12 for the stent graft system 1. In various embodiments, a cylindrical device 30 with open ends is used to hold the stent graft system 1 as the release wire 12 is installed.

Figure 8:
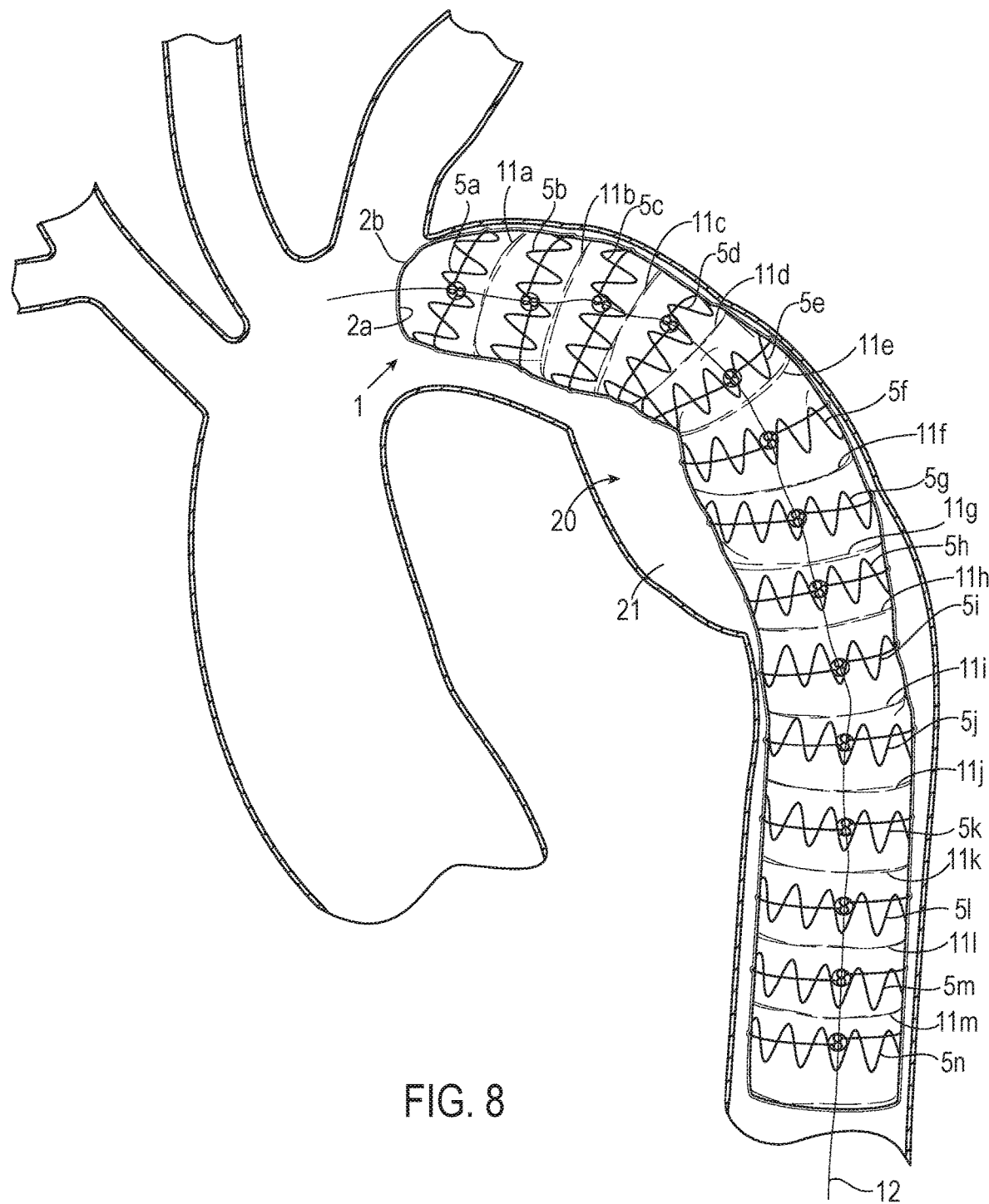
FIG. 8 shows a stent graft system in accordance with an embodiment inserted in a blood vessel and in a compressed state.
Figure 9:
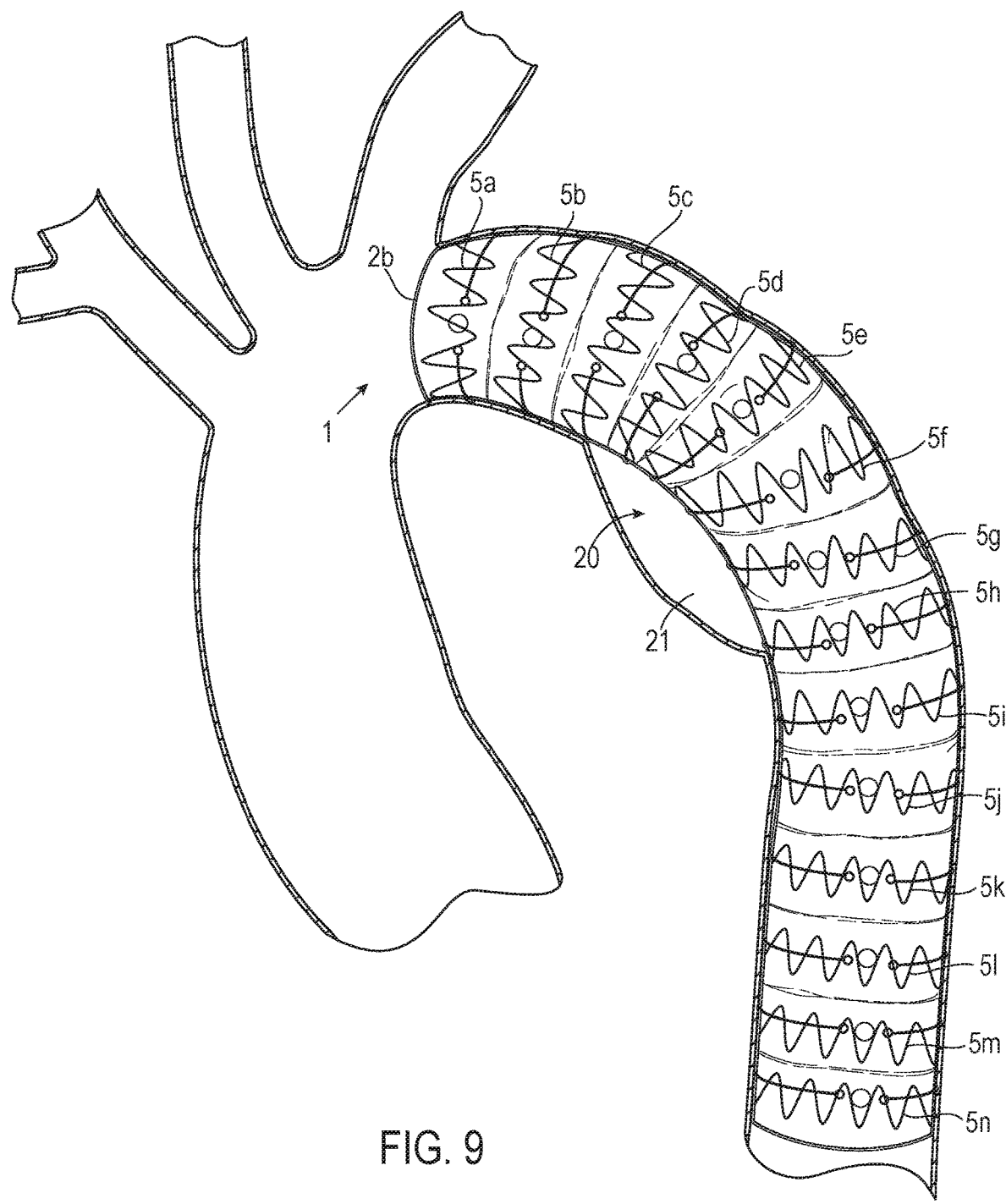
FIG. 9 shows a stent graft system in accordance with an embodiment inserted in a blood vessel and in an uncompressed state.

FIG. 8 shows an example of the stent graft system 1 of FIG. 1 in a compressed state being deployed in a blood vessel, such as an aorta 20. FIG. 9 shows an example of the stent graft system 1 in an expanded state upon deployment in the aorta 20. FIG. 10 shows a flowchart of a method in accordance with an embodiment for deploying a stent graft system, such as the stent graft system 1 of FIG. 1, in a blood vessel. The method shown in FIG. 10 allows for using a stent graft system that includes a first layer of graft material, a second layer of graft material, a plurality of stent members, and a plurality of reducing belts.

With reference to FIGS. 1, 8, and 10, in step 200, the stent graft system is positioned in a blood vessel with each stent member of the plurality of stent members held in a compressed state by a corresponding reducing belt of the plurality of reducing belts that is located at least partially in a corresponding channel between the second layer of graft material and the first layer of graft material. For example, the stent graft system 1 having reducing belts 6a, 6b, 6c, 6d, 6e, 6f, 6g, 6h, 6i, 6j, 6k, 6l, 6m, 6n is positioned in the aorta 20 where the reducing belts 6a, 6b, 6c, 6d, 6e, 6f, 6g, 6h, 6i, 6j, 6k, 6l, 6m, 6n are in the corresponding channels 3a, 3b, 3c, 3d, 3e, 3f, 3g, 3h, 3i, 3j, 3k, 3l, 3m, 3n around the corresponding stent members 5a, 5b, 5c, 5d, 5e, 5f, 5g, 5h, 5i, 5j, 5k, 5l, 5m, 5n of the stent graft system 1 between the first layer of graft material 2a and the second layer of graft material 2b.

In various embodiments, the stent graft system 1 allows for controlled accurate deployment that allows for repositionability. The creases for the pleats 11a, 11b, 11c, 11d, 11e, 11f, 11g, 11h, 11i, 11j, 11k, 11l, 11m between the corresponding stent members 5a, 5b, 5c, 5d, 5e, 5f, 5g, 5h, 5i, 5j, 5k, 5l, 5m, 5n in various embodiments make it easier to curve the stent graft system 1 within the aorta 20 as shown in FIG. 8. The stent graft system 1 can be positioned to repair the aorta 20 across an aneurysm 21.

With reference to FIGS. 1, 8, 9, and 10, in step 210, the plurality of reducing belts are released to permit the plurality of stent members to expand from the compressed state to an uncompressed state that is an expanded state. In some embodiments, the releasing of the plurality of reducing belts includes the step 220 of pulling a release wire through and out of loops of one or more of the plurality of reducing belts. For example, the release wire 12 is pulled to release the reducing belts 6a, 6b, 6c, 6d, 6e, 6f, 6g, 6h, 6i, 6j, 6k, 6l, 6m, 6n around the stent members 5a, 5b, 5c, 5d, 5e, 5f, 5g, 5h, 5i, 5j, 5k, 5l, 5m, 5n and allow the stent graft system 1 to radially expand within the aorta 20 to go from the compressed state shown in FIG. 8 to the radially expanded and uncompressed state shown in FIG. 9. As shown in FIG. 9, the stent graft system 1 radially expands to contact at least a portion of wall of a blood vessel, such as a wall of the aorta 20, and allows for crossing an aneurysm, such as the aneurysm 21 in the aorta 20.

Figure 11:
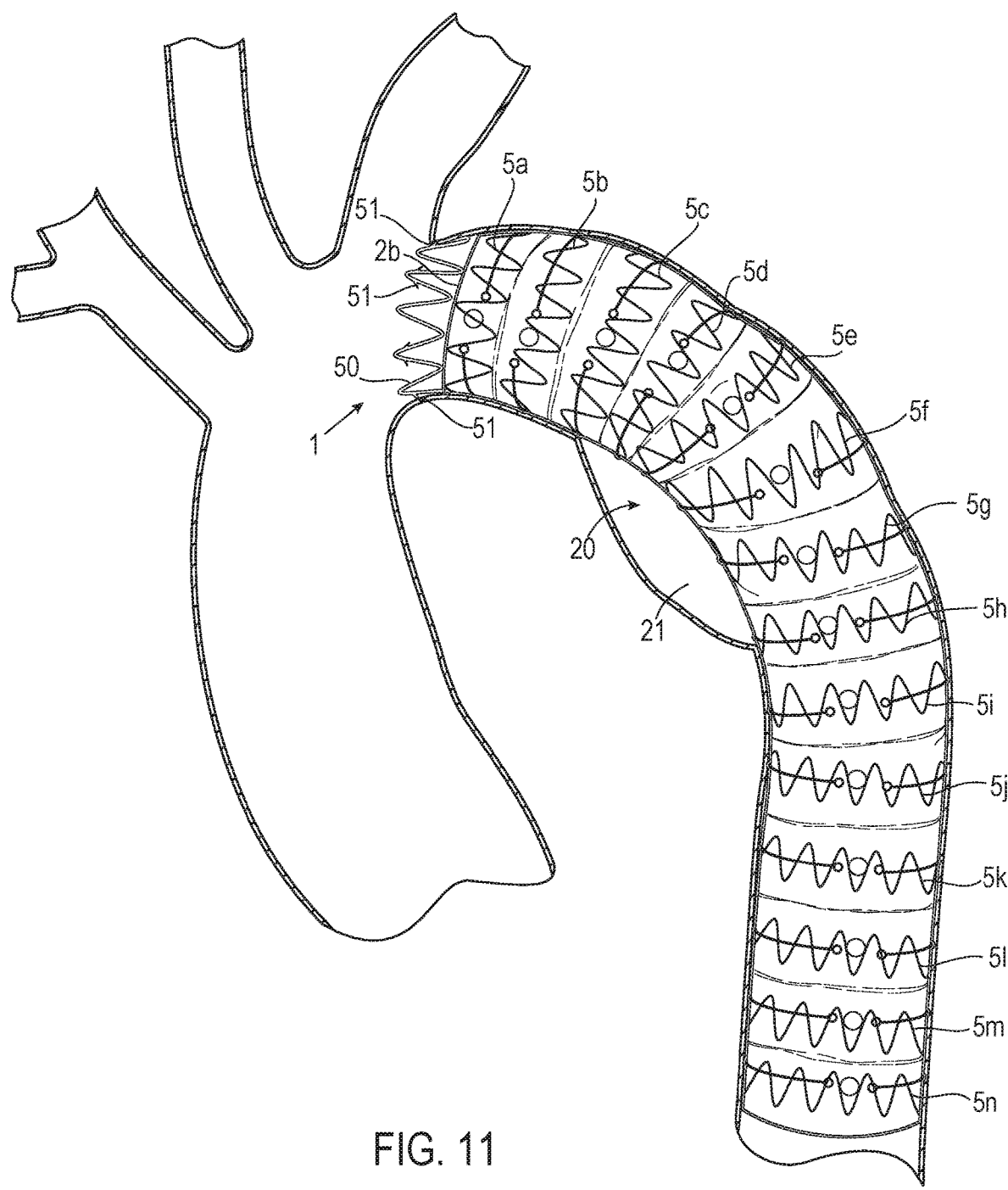
FIG. 11 shows a stent graft system in accordance with an embodiment inserted in a blood vessel and having an anchor stent for fixation.

FIG. 11 shows an embodiment of the stent graft system 1 in which the stent graft system 1 further includes a stent anchor 50 at a proximal end of the stent graft system 1. The stent anchor 50 allows for fixation of the stent graft system 1 in a blood vessel, such as in the aorta 20. In various embodiments, the stent anchor 50 includes barbs 51 or other fixation elements, and the stent anchor 50 is radially expandable from a compressed state to have the barbs 51 pierce a wall of the blood vessel, such as a wall of the aorta 20, when the stent anchor 50 expands to an expanded or uncompressed state.

With reference to FIGS. 1 and 2, the stent graft system 1 in accordance with an embodiment includes the first layer of graft material 2a, the second layer of graft material 2b, the stent member 5a, and the reducing belt 6a. The stent member 5a is located between the first layer of graft material 2a and the second layer of graft material 2b. The reducing belt 6a is located at least partially in the channel 3a between the second layer of graft material 2b and the first layer of graft material 2a and around at least a portion of the stent member 5a.

The second layer of graft material 2b has a shape that provides the channel 3a between the second layer of graft material 2b and the first layer of graft material 2a. In various embodiments, the reducing belt 6a of the stent graft system 1 of FIG. 1 has a length that is shorter than a circumference of the stent member 5a when the stent member 5a is fully expanded as in FIG. 9 but longer than a circumference of the stent member 5a when the stent member 5a is in a compressed state as in FIG. 8. With reference to FIGS. 1 and 2, in some embodiments, the reducing belt 6a includes the first loop 7a and the second loop 8a at the ends of the reducing belt 6a. Also, in some embodiments, the stent graft system 1 includes the release wire 12 passing through the first loop 7a and the second loop 8a of the reducing belt 6a.

The stent member 5a is radially expandable from a compressed state to an uncompressed state, and the reducing belt 6a is releasable to permit the stent member 5a to expand from the compressed state to the uncompressed state. The stent graft system 1 further includes the stent member 5b located between the first layer of graft material 2a and the second layer of graft material 2b, and the reducing belt 6b located at least partially in the channel 3b between the second layer of graft material 2b and the first layer of graft material 2a and around at least a portion of the stent member 5b.

The second layer of graft material 2b has a shape that provides the channel 3b between the second layer of graft material 2b and the first layer of graft material 2a. Also, in some embodiments, the reducing belt 6b includes the first loop 7b and the second loop 8b, and the stent graft system 1 includes the release wire 12 passing through the first loop 7a and the second loop 8a of the reducing belt 6a and through the first loop 7b and the second loop 8b of the reducing belt 6b. As shown in FIG. 9, in some embodiments the stent graft system 1 further includes a crease due to a pleat 11a in the second layer of graft material 2b between the stent member 5a and the second stent member 5b.

Figure 12:
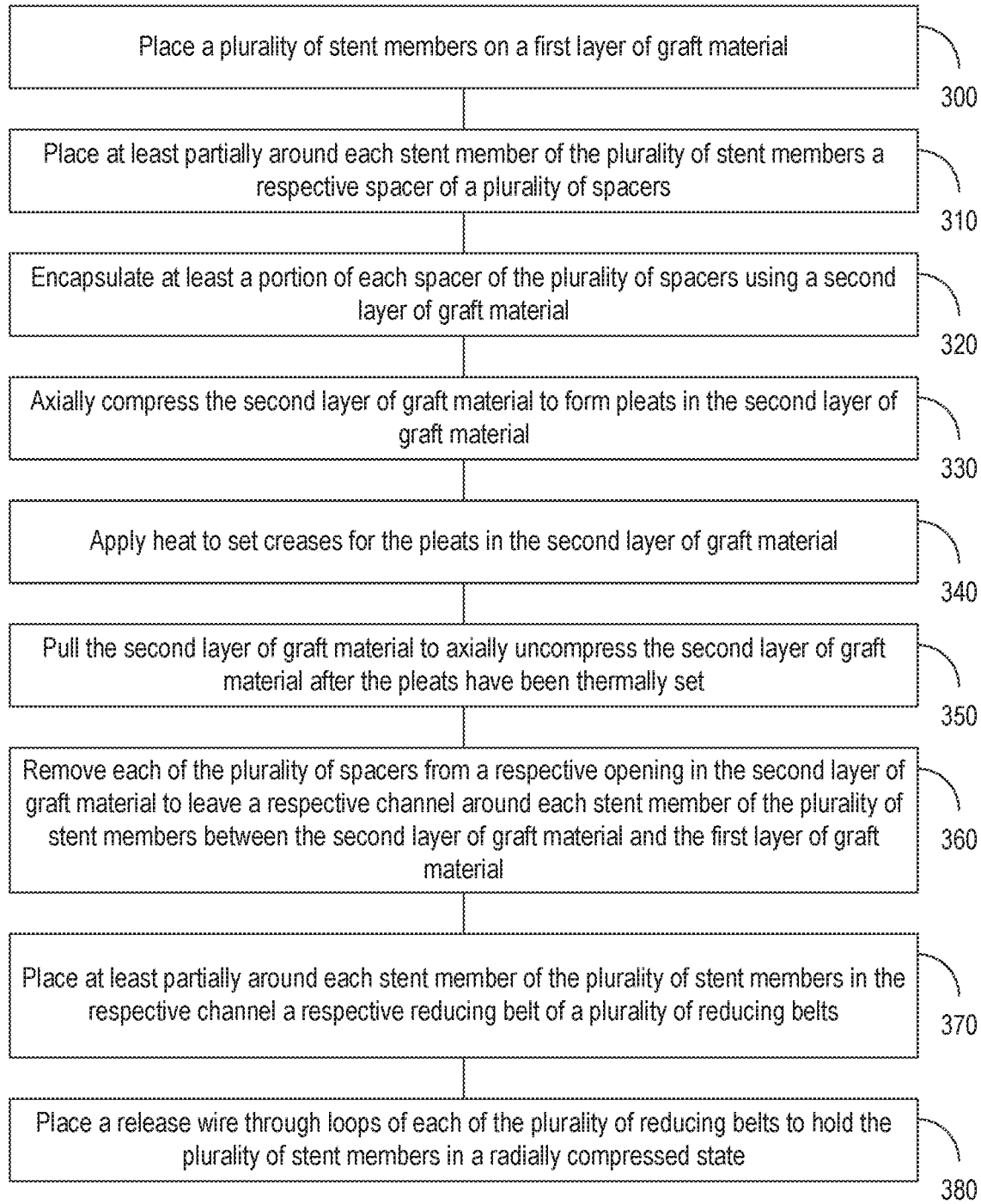
FIG. 12 is a flowchart of a method for making a stent graft system in accordance with an embodiment.

FIG. 12 is a flowchart of a method for manufacturing a stent graft system in accordance with an embodiment. In step 300, a plurality of stent members are placed on a first layer of graft material. In step 310, at least partially around each stent member of the plurality of stent members there is placed a respective spacer of a plurality of spacers. In step 320, at least a portion of each spacer of the plurality of spacers is encapsulated using a second layer of graft material.

In step 330, the second layer of graft material is axially compressed to form pleats in the second layer of graft material. In step 340, heat is applied to set creases for the pleats in the second layer of graft material. In some embodiments, the applying of the heat includes baking the second layer of graft material in an oven to set the creases for the pleats in the second layer of graft material. In step 350, the second layer of graft material is pulled to axially uncompress the second layer of graft material after the pleats have been thermally set. In step 360, each of the plurality of spacers is removed from a respective opening in the second layer of graft material to leave a respective channel around each stent member of the plurality of stent members between the second layer of graft material and the first layer of graft material. In various embodiments, each spacer of the plurality of spacers comprises a tube.

In step 370, at least partially around each stent member of the plurality of stent members in the respective channel is placed a respective reducing belt of a plurality of reducing belts. In some embodiments, each reducing belt of the plurality of reducing belts comprises thread. In some embodiments, each reducing belt of the plurality of reducing belts comprises a natural or synthetic fiber. In some embodiments, each reducing belt of the plurality of reducing belts comprises metal. In some embodiments, each of the plurality of reducing belts includes loops. In step 380, a release wire is placed through loops of each of the plurality of reducing belts to hold the plurality of stent members in a radially compressed state. In some embodiments, the reducing belts are positioned such that ends of each reducing belt of the plurality of reducing belts extend out of a respective opening in the second layer of graft material.

In various embodiments, a release wire extends through a stent graft system to lock reducing belts, such as sutures or the like, in place surrounding stent members. The release wire may then be removed from loops of the sutures to release the sutures and allow for expansion of the stent members. Upon expansion of the stent members, the stent graft system provides a radially outward force on the walls of an aorta. In various embodiments, the stent graft system acts to reinforce the walls of a weakened artery, such as may be caused by an aneurysm.

In various embodiments, during manufacturing of a stent graft system, a first layer of graft material and stent members are surrounded with tubing. Then, the stent members, the first layer of graft material, and the tubing are encapsulated with an additional layer of graft material, creating channels between the two layers of graft material where the tubing lies within the channels. In various embodiments, the layers of graft material are thermally pleated using heat. In various embodiments, the tubing is removed from between the layers of graft material, which leaves a channel over each of the stent members. In some embodiments, sutures are placed around each stent member in the corresponding channel between layers of graft material to replace the tubing and retain the compression of the stent members. In various embodiments, a release wire is inserted through loops of the sutures, running from a distal end to a proximal end of the stent graft system, to lock the sutures in place and maintain compression of the stent members. In various embodiments, pulling the release wire releases the sutures, allowing the stent members to expand. The release wire may be removed after insertion of the stent graft system into a patient to the correct location within an artery, such as within an aorta.

In various embodiments, the stent members may be attached to or laminated to one or more layers of graft material. In various embodiments, the stent members are fully laminated or fused within the one or more layers of graft material. In some embodiments, the stent members are partially laminated or free-floating within or between one or more layers of graft material. In some embodiments, the layers of graft material extend the entire length of the stent graft system, from a proximal end to a distal end. In some other embodiments, the layers of graft material do not cover the entire length of the stent graft system, leaving a portion of the distal and/or the proximal end exposed, which may leave some stent members exposed at either end.

In various embodiments, during manufacture there is tubing surrounding the stent members. In various embodiments, each stent member has a separate piece of tubing that surrounds the stent member circumferentially. In some embodiments, the pieces of tubing may connect at various points. In some embodiments, the tubing may consist of a single piece wrapped spirally around some or all of the stent members. In various embodiments, stent members are at least partially laminated between layers of graft material.

In various embodiments, during manufacturing, longitudinal compression of the stent graft system from a longitudinally extended configuration to a compressed configuration followed by thermal pleating creates a plurality of circumferential pleats of a predetermined orientation such that pleated sections of the stent graft system nest within each other along an axis. In various embodiments, circumferential pleats in any orientation may be thermally pleated to lock the pleats in that orientation such that when the stent graft is longitudinally compressed again or angled in a natural setting, for example, after implantation of the stent graft system, the compressed stent graft will memorize and resume the preset pleat orientation.

In various embodiments, a release wire passes through loops on every suture around every stent member and therefore compresses each stent member. In various other embodiments, the release wire may pass through loops of sutures on only a portion of stent members. Some embodiments may have multiple release wires, each for releasing reducing belts around a corresponding subset of the stent members. In various embodiments, the release wire acts as a locking mechanism, causing sutures to tightly remain in a circumferentially surrounding position around the stent members until the release wire is pulled. In various embodiments, when the release wire is removed from sutures, loops of the sutures are freed and the sutures no longer tightly surround the stent members, allowing the stent members to uncompress into a radially expanded state.

In various embodiments, a stent graft system in accordance with an embodiment is deployed in an aortic arch. In some embodiments, a stent graft system in accordance with an embodiment is inserted into the descending aorta portion of an aorta. In various embodiments, a stent graft system has stent members that are configured to allow the stent graft system to bend to conform to the shape of an aorta. In various embodiments, upon expansion of the stent members, the stent graft system provides a radially outward force on the walls of the aorta. In various embodiments, the stent graft system includes branched portions to extend into one or more additional blood vessels.

Various embodiments provide for improved compression and controlled expansion of a stent graft system upon deployment within a patient. Reducing belts circumferentially surround stent members of the stent graft system. In some embodiments, a release wire is threaded through loops of the reducing belts extending from channel openings in graft material and the release wire extends on both ends of the stent graft system. Removal of the release wire loosens the reducing belts to allow the stent members of the stent graft system to fully expand. The reducing belts and the release wire allow for a controlled and accurate deployment of the stent graft system in one or more blood vessels.

A stent graft system in accordance with an embodiment includes a first layer of graft material, a second layer of graft material, one or more stent members, one or more reducing belts, and a release wire. In various embodiments, the one or more stent members are located between the first layer of graft material and the second layer of graft material, and the second layer of graft material is formed to provide a corresponding channel around each of the one or more stent members. In various embodiments, the one or more reducing belts each have a loop at both ends and are each located in a corresponding channel around a corresponding one of the stent members, and have a length that is shorter than a circumference of the corresponding stent member when the corresponding stent member is fully expanded but longer than a circumference of the corresponding stent member when the stent member is in a compressed state. In various embodiments, the release wire passes through both loops of each of the one or more reducing belts when the one or more stent members are in a compressed state.

The embodiments disclosed herein are to be considered in all respects as illustrative, and not restrictive of the invention. The present invention is in no way limited to the embodiments described above. Various modifications and changes may be made to the embodiments without departing from the spirit and scope of the invention. Various modifications and changes that come within the meaning and range of equivalency of the claims are intended to be within the scope of the invention.

What is claimed is:

1. A stent graft system, comprising:
a first layer of graft material;
a second layer of graft material;
a stent member located between the first layer of graft material and the second layer of graft material; and
a reducing belt located at least partially in a channel between the second layer of graft material and the first layer of graft material and extending circumferentially around at least a portion of the stent member to hold the stent member in a radially compressed state,
wherein first end of the belt is secured to a second end of the belt, and
wherein the second layer of graft material is continuous over an axial length extending at least three rings of the stent member.

2. The stent graft system of claim 1,
wherein the second layer of graft material has a shape that provides the channel between the second layer of graft material and the first layer of graft material.

3. The stent graft system of claim 1,
wherein the reducing belt has a length that is shorter than a circumference of the stent member when the stent member is fully expanded but longer than a circumference of the stent member when the stent member is in a compressed state.

4. The stent graft system of claim 1,
wherein the reducing belt includes a first loop at the first end and a second loop at e second end.

5. The stent graft system of claim 4, further comprising:
a release wire passing through the first loop and second loop of the reducing belt.

6. The stent graft system of claim 1,
wherein the stent member is radially expandable from a compressed state to an uncompressed state; and
wherein the reducing belt is releasable to permit the stent member to expand from the compressed state to the uncompressed state.

7. The stent graft system of claim 1, further comprising:
a second stent member located between the first layer of graft material and the second layer of graft material; and
a second reducing belt located at least partially in a second channel between the second layer of graft material and the first layer of graft material and around at least a portion of the second stent member.

8. The stent graft system of claim 7,
wherein the second layer of graft material has a shape that provides the second channel between the second layer of graft material and the first layer of graft material.

9. The stent graft system of claim 7,
wherein the reducing belt includes loops and the second reducing belt includes loops; and
wherein the stent graft system further comprises a release wire passing through the loops of the reducing belt and through the loops of the second reducing belt.

10. The stent graft system of claim 7, further comprising:
a pleat in the second layer of graft material between the stent member and the second s member.

11. A stent graft system, comprising:
a first layer of graft material;
a second layer of graft material;
a stent member comprising a plurality of annular rings located between the first layer of graft material and the second layer of graft material; and
a reducing belt located at least partially in a channel between the second layer of graft material and the first layer of graft material and extending circumferentially around at least a portion of the stent member to hold the stent member in a radially compressed state,
wherein first end of the belt is secured to a second end of the belt, and
wherein each annular ring has a respective and separate reducing belt.

12. A stent graft system, comprising:
a first layer of graft material;
a second layer of graft material;
a stent member comprising a plurality of annular rings located between the first layer of graft material and the second layer of graft material; and
a reducing belt located at least partially in a channel between the second layer of graft material and the first layer of graft material and extending circumferentially around at least a portion of the stent member to hold the stent member in a radially compressed state,
wherein a first end of the belt is secured to a second end of the belt, and
wherein the second layer of graft material is formed to have a shape that provides a channel around the apex of at least one ring of the stent member.

* * * * *